United States Patent [19]

Paradis

[11] Patent Number: 4,541,452
[45] Date of Patent: Sep. 17, 1985

[54] SOLVENT PRESSURIZATION SYSTEM

[75] Inventor: Roland C. Paradis, Newtown, Conn.

[73] Assignee: The Perkin-Elmer Corporation, Norwalk, Conn.

[21] Appl. No.: 659,374

[22] Filed: Oct. 10, 1984

[51] Int. Cl.⁴ .............................................. B01D 15/08
[52] U.S. Cl. .................................. 137/209; 210/198.2; 55/386
[58] Field of Search ........................... 137/209, 561 R; 210/198.2, 656, 659; 55/386

[56] References Cited

U.S. PATENT DOCUMENTS 4,133,767  1/1979  Bakalyar .................. 210/659 X
4,448,684  5/1984  Paradis .................... 210/198.2

Primary Examiner—Alan Cohan
Attorney, Agent, or Firm—E. T. Grimes; J. D. Crane

[57] ABSTRACT

The present invention is directed to a solvent pressurization system for use in liquid chromatography which includes a source of pressurized gas, a plurality of sealed vessels that are adapted to hold solvents therein, each of the vessels having a gas input port, said vessels being located within a closable compartment; a double manifold having a distribution chamber in communication with the pressurized gas from the gas source and an exhaust chamber communicatable with a venting system, a set of fittings for each vessel for controlling the gas flow from the distribution chamber to the vessel and from the vessel to the exhaust chamber, each set of fittings including inlet valve means and outlet valve means and an element for opening or closing both valve means together. The pressurization system further includes a system for releaving the pressure from the vessels when the compartment door is open, and a system for releaving the pressure from the vessels when the pressure in the vessels exceeds a predetermined pressure.

7 Claims, 4 Drawing Figures

FIG. 3A  OPERATIONAL POSITION

DE-COUPLED POSITION

SOLVENT PRESSURIZATION SYSTEM

FIELD OF THE INVENTION

The present invention generally relates to a system for pressurizing a plurality of vessels and, in particular, relates to a system for pressurizing a plurality of solvent vessels in a liquid chromatographic instrument.

This application is closely related to U.S. Pat. No. 4,448,684. This patent and the present application are both assigned to a common Assignee. The disclosure in said patent is incorporated herein by reference.

BACKGROUND OF THE INVENTION

In recent years liquid chromatography systems have evolved such that unattended analysis involves separating a particular sample a number of times but using a different solvent composition, or mixture each time. Alternately, a variety of different samples can be analyzed, each with a different solvent composition. In such systems, in order to enhance the flow of individual solvent components, it is helpful to individually pressurize each solvent container. Thus, when that solvent component is required by the liquid chromatography system the solvent readily flows from the container due to the pressure thereon rather than being flow regulated by a suction created in a piston cylinder. A major advantage to pressurizing the solvent components is that air bubbles, usually found in nonpressurized systems, are eliminated. Consequently, since air bubbles tend to reduce the performance of the solvent pump, the entire liquid flow exhibits an increased efficiency. However, since many solvents are acids or other hazardous materials and since any liquid under pressure is potentially injurious to both equipment and personnel, a number of potential dangers exist in present liquid chromatography solvent gradient systems.

One potential danger exists in the accessibility of the solvents, in particular, when those solvents are pressurized. The conventional approach to avoiding this danger is to provide a simple interlock which locks the access door to the solvent compartment whenever any solvent is pressurized. Unfortunately, most simple interlocks can be simply bypassed or manually overridden.

Another danger exists from system leakage. Leakage of solvent material or the leakage of external air into the system can have serious consequences. For example, the leakage of solvent material, such as an acid, from the system to, say, the laboratory workbench presents a danger to both personnel and equipment. Another consequence of leakage, perhaps of lesser danger to personnel but nevertheless serious, is unequal pressurization among the various solvent containers. Unequal pressurization among the solvent containers generally results in misproportioning of the solvent components in the resultant solvent mixture.

In consideration of the above, it is highly desirable to provide a solvent pressurization system which substantially, if not completely, alleviates these dangers.

SUMMARY OF THE INVENTION

Briefly, the present invention is directed to a new and improved solvent pressurization system for use in liquid chromatography, which includes a source of pressurized gas, a plurality of sealed vessels which are adapted to hold solvents therein, each of the sealed vessels having a gas input port and each of the vessels being located within a closable compartment. In addition the system of the present invention includes a double manifold having a distribution chamber in communication with the pressurized gas from the gas source and an exhaust chamber communicatable with venting means. A set of fittings for each vessel is provided for controlling the gas flow from the distribution chamber to its vessel and from the vessel to the exhaust chamber. Each set of fittings includes inlet valve means and outlet valve means and an element for opening or closing both valve means together.

According to one feature of the invention, the solvent pressurization system further includes means for releaving pressure comprising a piston exposed to the pressure of said exhaust chamber, said piston being movable between a first position wherein said exhaust chamber is in fluid flow communication with the venting means and a second position wherein said exhaust chamber is out of communication with the inventing means. The piston has a protuberance, which is engageable with the compartment door, to move said piston between its positions responsive to the opening or closing of the door. Further, this same piston serves as means for depressurizing the vessels when the pressure within the vessels exceeds a preselected venting pressure.

There has thus been outlined rather broadly the more important features of the invention in order that the detailed description that follows may be better understood, and in order that the present contribution to the art may be better appreciated. There are, of course, additional features of the invention that will be described more fully hereinafter. Those skilled in the art will appreciate that the conception on which this disclosure is based may readily be utilized as the basis of the designing of other systems for carrying out the various purposes of the invention. It is important, therefore, that this disclosure be regarded as including such equivalent systems as do not depart from the spirit and scope of the invention.

One embodiment of the invention has been chosen for purposes illustration and description and is shown in the accompanying drawings forming a part of the specification.

BRIEF DESCRIPTION OF THE DRAWINGS

FIG. 3A is an enlarged transverse sectional view showing one of the valve assemblies mounted on the manifold in its operational position.

DETAILED DESCRIPTION OF A PRESENTLY PREFERRED EMBODIMENT

Figure 1:
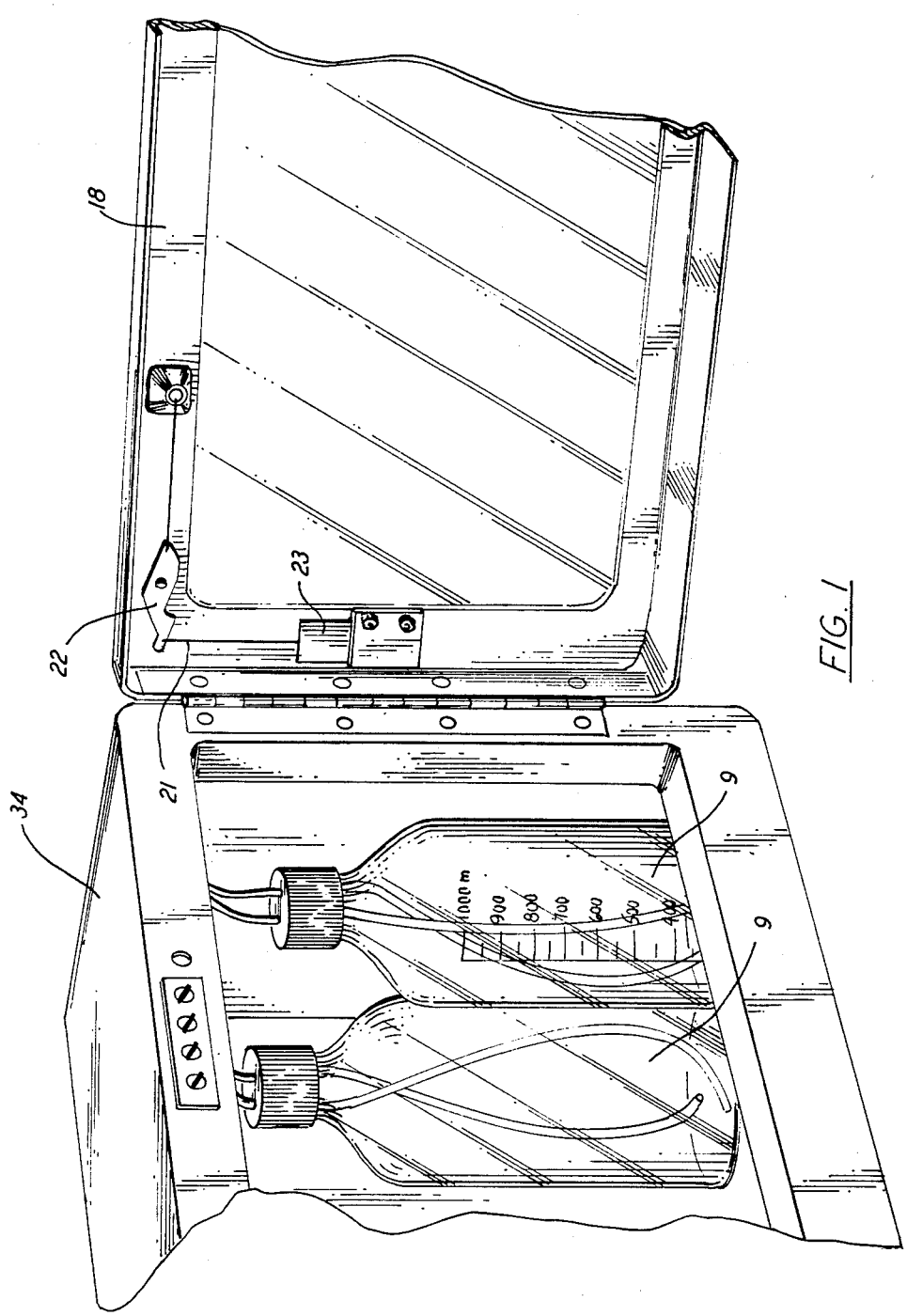
FIG. 1 is a side elevation showing solvent vessels within a closable compartment.
Figure 2:
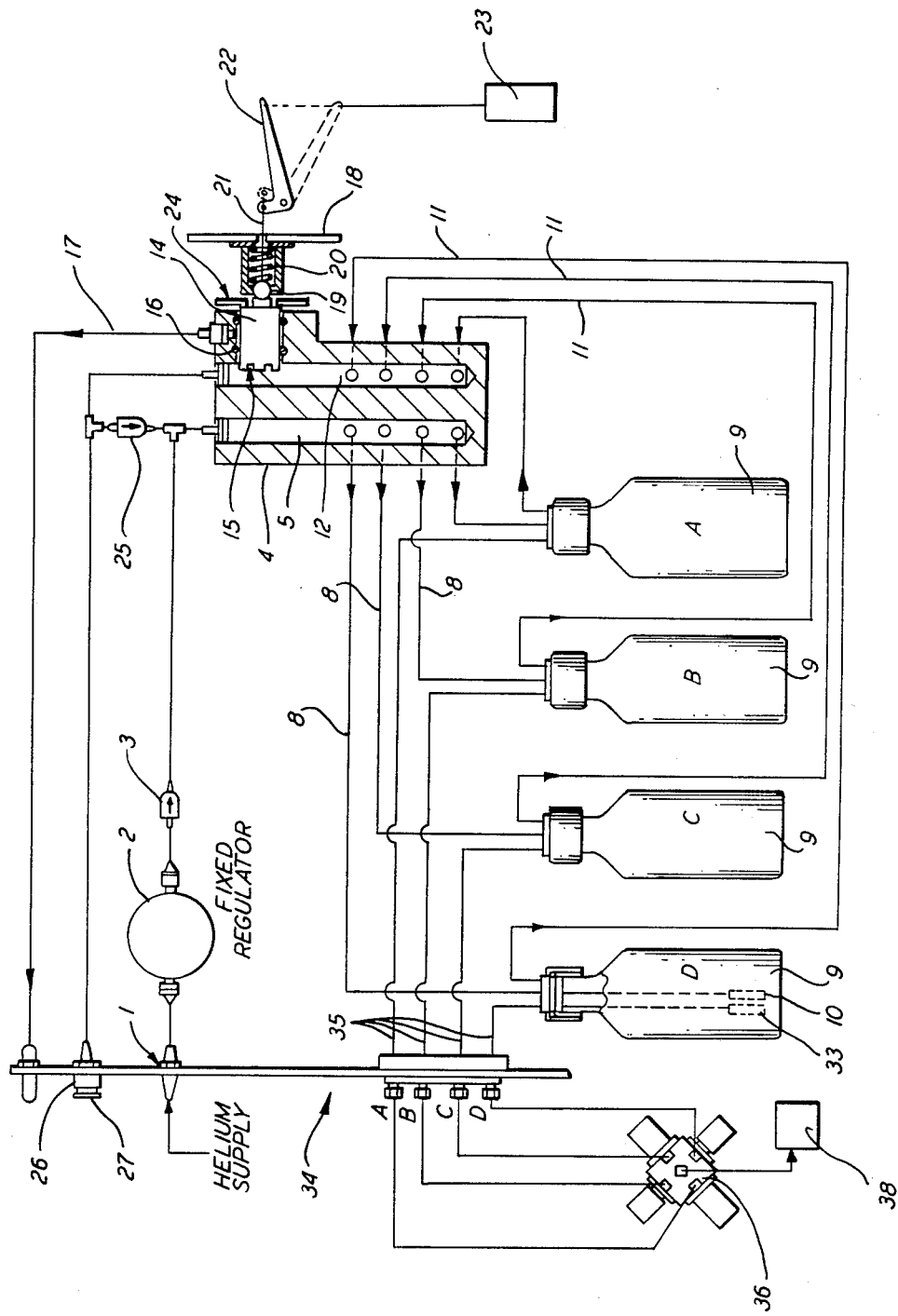
FIG. 2 is a schematic block diagram of a solvent pressurization system constructured according to the principles of the present invention.

The solvent pressurization system embodying the principles of the present invention is a stand alone solvent environmental control unit used for the pressurization and/or degassing of liquid chromatography solvents. In the exemplary embodiment four solvent vessels or bottles 9, FIGS. 1 and 2, are enclosed in a compartment or cabinet 34 to permit safe pressurizing of the bottles. For safety reasons, pressurizing capability is interlocked with the closing of the compartment door.

Opening of the door 18 results in automatic depressurizing and the starting of sparging for degassing of the solvents, as will be discussed more fully hereinafter. The solvent pressurization system has two primary operating modes. During one operating mode the solvent vessels 9 are pressurized and solvent is delivered via a multi-port proportioning valve 36 to a chromatographic pump 38. This mode is hereinafter referred to as the delivery mode. During the other operating mode, gas is passed through the solvents for the purpose of removing air bubbles therefrom, i.e. commonly known as degassing or sparging.

In the solvent pressurization system, a supply of helium enters through a bulkhead fitting 1 on the back panel of the cabinet 34. The helium enters a regulator 2 at a suitable primary pressure such as, for example, about 50 p.s.i. and exits therefrom at a pressure such as, for example, about 5 p.s.i. secondary pressure. It will be appreciated that the regulator is fixed and can not be inadvertently adjusted by the operator. It will only change, for example, about plus or minus 1 p.s.i. secondary pressure for plus or minus 20 p.s.i. of primary pressure change.

Figure 3B:
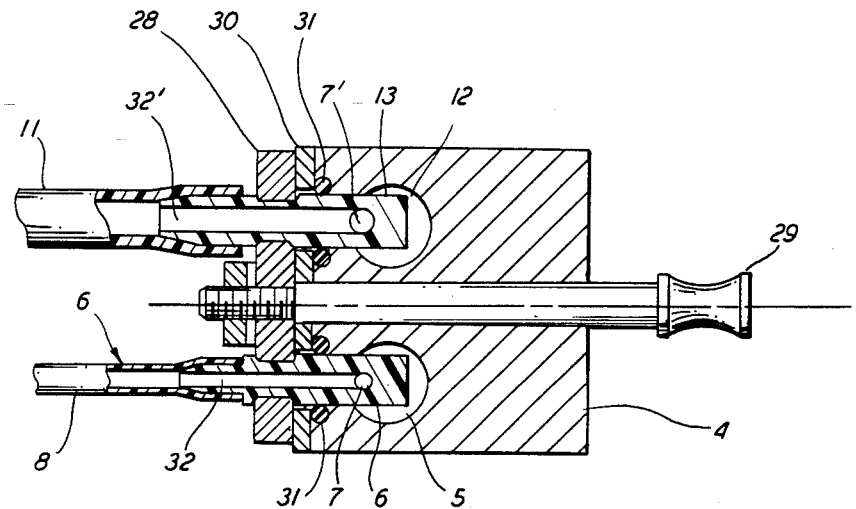
FIG. 3B is an enlarged transverse sectional view similar to FIG. 3A, but showing the valve assembly in its decoupled position.

As best seen in FIG. 2, the gas continues through a check valve 3 and into a distribution chamber 5 of a double manifold 4. This input check valve 3 is required to prevent solvent back up should depressurization take place in the supply side while there exists a pressure in the bottles. That is, if the system has been operating long enough for pressure to build up to say 5 p.s.i. for example at the top of the bottle 9 and the helium supply is then disconnected, the pressure would then drop to zero only as far as the check valve. The 5 p.s.i. pressure would be maintained throughout the remainder of the system by the check valve. If there was no check valve present, the pressure would drop to zero all the way down to the filter in the solvent. In that case the pressure in the bottle would force the solvent back up through the filter and all the way through the regulator and right out of the system. In addition, the check valve 3 also prevents flow back of the helium and vapors through the regulator 2. FIGS. 3A and 3B each show a cross-section of the manifold taken through both chambers and one set of fittings, which is the same for all four bottles. FIG. 3A shows the fittings in their operational position and FIG. 3B shows the same fittings in their decoupled position or mode. Referring in particular to FIG. 3A, from the chamber 5 the gas enters fitting or pin 6 through a radial hole or bore 7 in the pin when the valve is in its operational mode. The gas continues along an axial bore 32 in the pin into a polyethylene tube 8, which is pushed over the pin 6 and sealed therewith by virtue of its elastomeric properties.

Figure 3B:
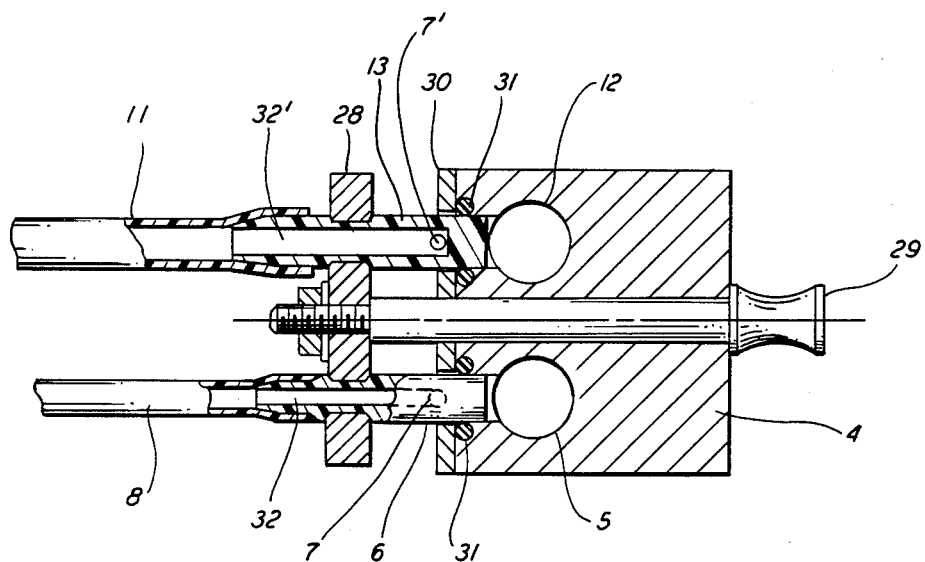

As seen in FIG. 2, the gas travels down the tubes 8 to the bottles 9 and then is discharged through a porous cylinder 10 at the bottom of the bottle, where it sparges through the solvent and rises to the top. This helium exits at the top of the bottle 9 and travels through a tube 11 and enters an exhaust chamber 12, FIG. 3, through an axial bore 32' in a pin 13 having a radial hole or bore 7'. If the door 18 of the cabinet 34 is open, the helium pushes a piston 14, FIG. 2, back until its slotted edge 15 moves past an "O" ring 16, and then the helium runs out a vent line 17. Sparging will continue, degassing the solvents as long as the door remains open or until the pressure is shutoff. When the door 18 is closed, the helium continues to sparge until the full regulated pressure of 5 p.s.i. is reached and then the helium will stop entering.

Still referring to FIG. 2, when the door is closed, a ball plunger 19 and spring 20 come to rest against the piston 14, restricting its motion. With the slots 15 restrained in front of the "O" ring 16 the helium can not communicate with the vent line 17 and the pressure builds up until about 5 p.s.i. is reached. Thus, with the access door 18 closed and consequently the venting line 17 sealed from the exhaust chamber 12, gas flow from the vessels 9 under normal operating conditions is prevented. Since gas flow from the vessels 9 is blocked, the gas pressure rises within the vessels to force the solvent therefrom via filters 33, through output conduits 35, respectively, and then to the multi-port proportioning valve 36. The spring 20 has a constant which is selected such that, if the regulator fails and becomes open to primary pressure, the piston slots 15 move past the "O" ring 16 and vent the system at a suitable pressure such as, for example, between about 7 and about 13 p.s.i. which is a safe maximum pressure. The same feature can also be used to indicate the pressure. For this purpose, a dial cord 21 is attached to the ball plunger 19 to follow the piston travel. The other end of the cord is attached to a pivoting lever 22, which also serves to multiply the motion by a preselected ratio. An indicator flag 23 is conveniently mounted for viewing from the front of the cabinet 34 and is calibrated, as desired.

When the door 18 is opened, the piston restriction is removed and the piston travels back to a stop plate 24, FIG. 2, and the pressure quickly drops back to zero. This serves as the required safety interlock, which prevents pressurizing with the door open. If accurate pressure monitoring is desired, a bulkhead connector 26, FIG. 2, is provided on the back panel of the cabinet or compartment 34 for that purpose. To use, the port sealing plug 27 is removed and the pressure gauge is attached.

The system includes a feedback check valve 25, FIG. 2, to prevent differential pressure from occurring between the input chamber 5 and the exhaust chamber 12. Thus, the feedback check valve is used to equilibrate the pressure between P1, the pressure between the input check valve 3 and the solvent in the bottle 9, and P2, the pressure above the solvent in the bottle. The pressure above the solvent in the bottle has been shown to rise due to an increase in temperature and/or due to the diffusion of the helium in the helium lines 8 leading to the bottles.

Heretofore, the removal of a bottle 9 from the system required actually taking out the bottle and then plugging the ends of the tubes left hanging therefrom. Another prior art way of removing the bottles from the system was to have a shut off valve mounted in each of the lines. However, not only are separate valves expensive, but they can be dangerous. For example, if the vent valve on a bottle is closed, and the pressure input valve is left open, an over pressure condition could exist in the bottle with no way of it being releaved. Conversely, the pressure input line could be closed and the vent line left open, then the pressure would again be in the bottle trying to force solvent up the solvent delivery line to the solvent proportioning valve.

According to the present invention, the valve means for the helium input line 8 and the valve means for the vent line 11 are tied together so that manipulation of a single element or plunger opens or closes both valve means together. FIG. 3A shows the valving arrangement in its operational mode and FIG. 3B shows it in its decoupled mode. A latch plate 28 ties the input pin 6 and the corresponding vent pin 13 together. This latch plate is attached to a push-pull knob 29 by means of a nut and lockwasher. A backing plate 30 keeps the "O" rings 31 compressed against the pins and thereby provides an effective seal. In the operational mode, the knob 29 is slid forward until the latch plate 28 rests against the backing plate 30 and the radial holes 7 and 7' in the pins 6 and 13 allows for the passage of the helium through the axial bores 32 and 32' and through the tubes 8 and 11 to and from the bottles. In the decoupled mode of FIG. 3B, the radial bores 7 and 7' are isolated from the chambers 5 and 12, thereby preventing gas flow to or from either chamber.

This convenient valving arrangement is also very useful for detecting leaks. Heretofore, it was very time consuming to find a leak in the pneumatic circuit. There were four bottles with three external connections per bottle. This represented twelve possible leak points which had to be checked. In the system of the present invention each bottle can be isolated, thereby reducing the possible number of leak points by a factor of four.

It will thus be seen that the present invention does indeed provide a new and improved solvent pressurization system which is both safe and efficient.

Although a certain particular embodiment of the invention has been herein disclosed for purposes of explanation, various modifications thereof, after study of the specification, will be apparent to those skilled in the art to which the invention pertains.

What is claimed is:

1. A solvent pressurization system for use in liquid chromatography, said system comprising:
   a source of pressurized gas;
   a plurality of sealed vessels, said vessels being adapted to hold solvents therein;
   each said vessel having a gas input port, said vessels being located within a closable compartment; and
   a double manifold having a distribution chamber in communication with said pressurized gas from said gas source and an exhaust chamber communicatable with venting means, a set of fittings for each vessel for controlling the gas flow from said distribution chamber to said vessel and from said vessel to said exhaust chamber, each set of fittings including inlet valve means and outlet valve means and an element for opening or closing both valve means together.

2. A solvent pressurization system according to claim 1 wherein said inlet valve means includes an inlet pin having a longitudinal bore in fluid flow communication with its corresponding vessel and a radial bore connected to the longitudinal bore which is open to said distribution chamber when said inlet valve means is open, and closed to said distribution chamber when said inlet valve means is closed, and wherein said outlet valve means includes an outlet pin having a longitudinal bore in fluid flow communication with said vent means and a radial bore connected to the longitudinal bore which is open to said exhaust chamber when said outlet valve means is open, and closed to said exhaust chamber when said outlet valve means is closed, and wherein said element includes a latch plate which mechanically ties said inlet pin to said outlet pin.

3. A solvent pressurization system according to claim 1 further comprising means for regulating the pressure to said vessel; said regulating means being fixed and unadjustable by an operator.

4. A solvent pressurization system according to claim 1 wherein said compartment has a compartment door, and said system further comprises means for releaving said pressure from said vessels when said compartment door is open.

5. A solvent pressurization system according to claim 4 wherein said means for releaving pressure comprises a piston exposed to the pressure of said exhaust chamber, said piston being movable between a first position wherein said exhaust chamber is in fluid flow communication with said venting means and a second position wherein said exhaust chamber is out of communication with said venting means, said piston having a protuberance engageable with said door to move said piston between said positions responsive to the opening or closing of said door.

6. A solvent pressurization system according to claim 1 further comprising means for depressurizing said vessels when the pressure within said vessels exceeds a preselected venting pressure.

7. A solvent pressurization system according to claim 6 wherein said means for depressurizing comprises a piston exposed to the pressures of said exhaust chamber, said piston being movable between a first position wherein said exhaust chamber is in fluid flow communication with said venting means and a second position wherein said exhaust chamber is out of communication with said venting means, spring means engaging said piston to move said piston between said positions responsive to the fluid pressure in said exhaust chamber.

* * * * *